(12) United States Patent
Ericson et al.

(10) Patent No.: US 7,776,842 B2
(45) Date of Patent: Aug. 17, 2010

(54) AMINO SUGAR CHELATES

(75) Inventors: Clayton Ericson, Morgan, UT (US); DeWayne Ashmead, Fruit Heights, UT (US); Stephen D. Ashmead, West Haven, UT (US); Amanda Rees, Bountiful, UT (US)

(73) Assignee: Albion Laboratories, Inc., Clearfield, UT (US)

( * ) Notice: Subject to any disclaimer, the term of this patent is extended or adjusted under 35 U.S.C. 154(b) by 966 days.

(21) Appl. No.: 11/466,701

(22) Filed: Aug. 23, 2006

(65) Prior Publication Data

US 2007/0049553 A1 Mar. 1, 2007

Related U.S. Application Data

(60) Provisional application No. 60/710,441, filed on Aug. 23, 2005.

(51) Int. Cl.
  *A61K 31/7008* (2006.01)
  *A61K 31/7012* (2006.01)
  *A61K 31/70* (2006.01)
  *A61K 31/715* (2006.01)

(52) U.S. Cl. .............. 514/62; 514/54; 514/23; 514/61; 514/53; 536/18.7; 536/123.1; 536/55.2

(58) Field of Classification Search .......... 514/62, 514/54, 23, 61, 53; 536/18.7, 123.1, 55.2
See application file for complete search history.

(56) References Cited

U.S. PATENT DOCUMENTS 6,476,005 B1 * 11/2002 Petito et al. .............. 514/62
2004/0254142 A1 * 12/2004 Kovler ..................... 514/54

2005/0037996 A1 * 2/2005 Beck et al. ............... 514/59

OTHER PUBLICATIONS

Deiana et al. (Journal of the Chemical Society, Dalton Transactions: Inorganic Chemistry (1972-1999) (1991), (5), 1237-41).*

* cited by examiner

*Primary Examiner*—Shaojia Anna Jiang
*Assistant Examiner*—Michael C Henry
(74) *Attorney, Agent, or Firm*—Ryan L. Marshall; Christopher L. Wight; Brinks Hofer Gilson & Lione

(57) ABSTRACT

The present invention includes amino sugar chelates and methods for preparing amino sugar chelates of the formula given below, where M is a metal; $R_2$ and $R_3$ are independently selected from H, OH and hydroxyl substituted $C_1$-$C_8$ alkyl; $R_4$ is selected from H, $CO_2H$, OH, and hydroxyl substituted $C_1$-$C_8$ alkyl; each $R_5$ is independently selected from H, OH, and hydroxyl substituted $C_1$-$C_8$ alkyl; A is selected from CH and O; a is from 0-6; b is from 0-6; n is from 1 to 8. The amino sugar chelates may include matrix stabilizing salts. The compounds and compositions disclosed can be used as nutritional supplements to impart health benefits.

(Formula II)

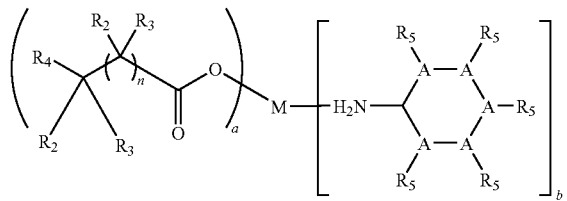

20 Claims, No Drawings

AMINO SUGAR CHELATES

CROSS REFERENCE TO RELATED APPLICATION

This application claims the benefit of the filing date of U.S. Provisional Patent Application Ser. No. 60/710,441, filed Aug. 23, 2005, the disclosure of which is incorporated, in its entirety, by this reference.

TECHNICAL FIELD OF THE INVENTION

The present invention relates to compositions of and methods of preparing amino sugar metal chelates.

BACKGROUND OF THE INVENTION

A longstanding but growing problem for humans and animals are afflictions affecting the connective tissue of joints, including arthritis and joint inflammation. Such afflictions are especially acute in joints such as the neck, back, arms, hips, ankles, and feet. Indeed, connective tissue afflictions are common, and can be both painful and debilitating.

One of the principal building blocks for growth and repair of connective tissue is a class of molecules called amino sugars. Amino sugars are assembled with other materials into proteoglycans. Proteoglycans provide the framework for collagen formation and also hold water to give connective tissues flexibility, resiliency, and resistance to compression. The biological pathways by which proteoglycans are incorporated into collagen include a rate-limiting step, a highly regulated control point beyond which there is a commitment to finish the bio-synthetic pathway. The inclusion of a rate-limiting step or steps permits more efficient regulation of complicated biosynthetic processes by the organism. For example, if conditions demand production and all the requisite raw materials are available, then stimulation of the rate-limiting step will cause the end product to be produced. To stop or slow production, the organism needs simply to regulate the rate-limiting step, usually by reducing one or more available precursors for the rate-limiting step.

In the production of proteoglycans, one rate-limiting step is the conversion of glucose to glucosamine. Glucosamine, an amino sugar, is an important precursor to access the various modified sugars necessary for production of proteoglycans including glucosamine sulfate, galactosamine, N-acetylglucosamine, and others. In vitro, the introduction of glucosamine has been demonstrated to increase the synthesis of collagen and glycosaminoglycans in fibroblasts, which is the first step in repair of connective tissues.

Amino sugars like glucosamine are also used in the treatment of rheumatic fever, arthosic complaints and treatment of pathological conditions originating from metabolic disorders of the osteo-articular tissue.

Administration of amino sugars and metals which are involved in connective tissue repair and growth is designed to enhance proteoglycan through concentration of glycosaminoglycans. Enhanced proteoglycan provides the framework for collagen and other joint components, as well as imparting flexibility, resiliency, and resistance to compression.

Chelates are beneficial sources of various nutritionally important components. The structure, chemistry, and bioavailability of many chelates have been documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.

Accordingly, the inventors herein describe compounds and compositions and methods of making the same which are designed to impart health benefits.

SUMMARY OF THE INVENTION

The present invention includes compositions of chelate complexes comprising a metal, one or more amino sugar ligands, one or more saturated hydroxylated carboxylic acid ligands, and nutritionally acceptable salts thereof. In some embodiments, the saturated hydroxylated carboxylic acid ligand is selected from one or more of aldonic acids, uronic acids and aldaric acids. In some embodiments, the metal is selected from magnesium, calcium, copper, zinc, iron, chromium, cobalt, molybdenum, selenium and manganese. In a more specific embodiment, the metal is manganese. In some embodiments, the amino sugar is selected from one or more of glucosamine, galactosamine, mannosamine, neuraminic acid, muramic acid, and glucuronamide. In a more specific embodiment, the amino sugar is glucosamine. In some embodiments, the saturated hydroxylated carboxylic acid is gluconic acid. In some embodiments, the chelated complexes are in a stabilizing matrix salt. In some embodiments, the stabilizing matrix salt is selected from one or more alkaline and alkaline earth metal salts of sulfates, carbonates, citrates, malates, and succinates. In more specific embodiments, the stabilizing matrix salt is magnesium sulfate and hydrochloric acid. In a more specific embodiment, the metal is manganese, the amino sugar is glucosamine, and the saturated hydroxylated carboxylic acid is gluconic acid.

In another aspect of the invention, an amino sugar chelate is provided comprising one or more amino sugar ligands, one or more saturated hydroxylated carboxylic acid ligands, and a metal, wherein the ligands and the metal have a molar ratio of from 1:1 to 4:1. Optionally, the amino sugar chelate is mixed in a stabilizing matrix salt. In some embodiments, the amino sugar chelate is a glucosamine chelate with one or more glucosamine ligands and manganese gluconate where the glucosamine ligand to manganese ratio is 2:1. In some embodiments, the amino sugar chelate can be defined by the formula: $(C_6H_{13}NO_5)_b M(C_6H_{12}O_7)_a$, wherein a is from 1 to 6, and b is from 1 to 6. In more specific embodiments, a is 1 and b is 2. In other specific embodiments, a is 2 and b is 2.

In another embodiment, a compound of the formula:

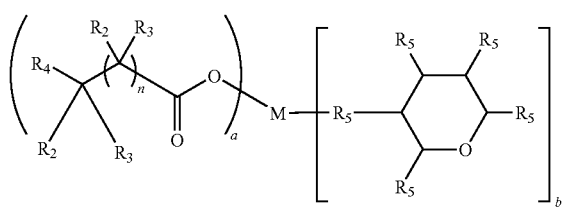

is provided where M is a metal, $R_2$ and $R_3$ are independently selected from H, OH, and hydroxyl substituted $C_1$-$C_8$ alkyl, $R_4$ is selected from H, $CO_2H$, OH, and hydroxyl substituted $C_1$-$C_8$ alkyl, each $R_5$ is independently selected from H, OH, $NH_2$, and hydroxyl substituted $C_1$-$C_8$ alkyl, at least one $R_5$ is $NH_2$, a is from 1-6, b is from 1-6, n is from 1 to 8, and nutritionally acceptable salts thereof.

In another embodiment, a compound of the formula:

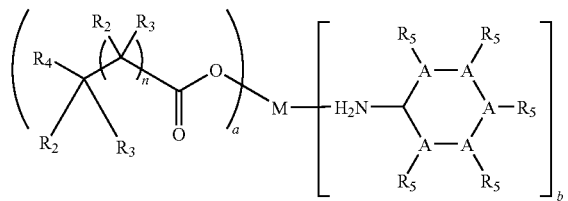

is provided where M is a metal, $R_2$ and $R_3$ are independently selected from H, OH and hydroxyl substituted $C_1$-$C_8$ alkyl, $R_4$ is selected from H, $CO_2H$, OH and hydroxyl substituted $C_1$-$C_8$ alkyl, each $R_5$ is independently selected from H, OH, hydroxyl substituted $C_1$-$C_8$ alkyl or absent, A is selected from CH and O, a is from 1-6, b is from 1-6, n is from 1 to 8, and nutritionally acceptable salts thereof. In some embodiments of the formulas, M is selected from magnesium, calcium, copper, zinc, iron, chromium, cobalt, molybdenum, selenium and manganese. In more specific embodiments, M is manganese. In some embodiments, $R_2$ and $R_3$ are independently selected from H and OH. In some embodiments a is 2. In some embodiments M is a manganese, each $R_2$ is OH, each $R_3$ is H, $R_4$ is $CH_2CH_2OH$, $R_5$ is independently selected from H, OH, hydroxyl substituted $C_1$-$C_8$ alkyl, or absent, each A is independently selected from CH, $CH_2$ and O, a is from 1-6, b is from 1-6 and n is 3.

In another embodiment, a compound of the formula:

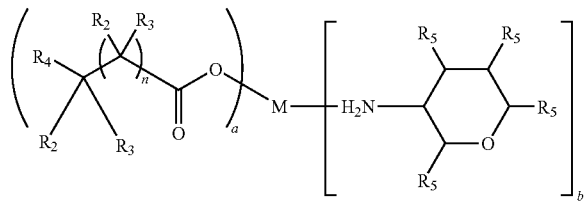

is provided wherein M is a metal, $R_2$ and $R_3$ are independently selected from H, OH, and hydroxyl substituted $C_1$-$C_8$ alkyl, $R_4$ is selected from H, OH, $CO_2H$, and hydroxyl substituted $C_1$-$C_8$ alkyl, each $R_5$ is independently selected from H, OH, hydroxyl substituted $C_1$-$C_8$ alkyl or absent, each A is independently selected from CH, $CH_2$ and O, a is from 1-6, b is from 1-6, n is independently from 0 to 8, and a stabilizing matrix salt.

In another aspect of the invention, compositions of the present invention include compounds described herein, and other optional ingredients. In some embodiments, the optional ingredient may be vitamin C. In some embodiments, the optional ingredient may be chondroitin.

In another aspect of the invention, a method of the present invention includes a method for preparing an amino sugar chelate comprising combining a metal or a metal salt with a solution, combining a saturated hydroxylated carboxylic acid with a solution, and combining an amino sugar with a solution where the solution has a pH of about 1 to about 7.5.

In one embodiment, the method of preparing an amino sugar chelate comprises combining a saturated hydroxylated carboxylic acid and a metal source in solution to obtain a metal saturated hydroxylated carboxylic acid salt and combining an amino sugar with the solution.

In another embodiment, the method of preparing an amino sugar chelate comprises mixing a metal source, a saturated hydroxylated carboxylic acid, and an amino sugar in a solution at a pH in the range of about 1 to about 7.5.

Optionally, the methods of the invention may include adding a matrix stabilizing salt to the solution.

Optionally, the methods of the invention may include adding a buffering agent selected from one or more of the group consisting of alkaline and alkaline earth metal salts of sulfates, carbonates, citrates, malates, and succinates to obtain a matrix of the buffering agent and the amino sugar chelate.

Optionally, the methods of the invention may include removing solvent from the solution. In yet another aspect of the invention, products of the methods of the invention are obtained.

DETAILED DESCRIPTION OF THE INVENTION

While the terminology used in this application is standard within the art, the following definitions of certain terms are provided to assure clarity.

Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "chelate" as used herein means a molecular entity made up of a central metal associated with at least one bidentate ligand and optionally associated with one or more mono- or multi-dentate ligands. In the interaction between the central metal and any of the ligands, the bonds between the ligand and the central metal can include covalent bonds, ionic bonds, and/or coordinate covalent bonds. Chelation can be confirmed and differentiated from mixtures of components by infrared spectra through comparison of the bond assignments from the unbound ligand to the chelate where bond formation occurs.

The term "chelate ring" as used herein means the atoms of the ligand and central metal which form a heterocyclic ring with the metal as the closing member. In the interaction between the central metal and a multidentate ligand, one or more chelate rings of from 3 to 8 members can exist. Typically, the chelate ring will be of from 5 to 6 members.

The term "ligand" as used herein means a molecular group that is associated with a central metal atom. The terms bidentate (or didentate), tridentate, tetradentate, and multidentate are used to indicate the number of potential binding sites of the ligand. For example, a carboxylic acid can be a bidentate or other multidentate ligand because it has at least two binding sites, the carboxyloxygen and hydroxyloxygen. In like manner, an amide has at least two binding sites, the carboxyloxygen and the nitrogen atom. An amino sugar can have at least two binding sites and many amino sugars will have multiple binding sites including the amino nitrogen, a hydroxyloxygen, an ethereal oxygen, an aldehyde carbonyl, and/or a ketone carbonyl.

The term "amino sugar" as used herein means monosaccharides having one alcoholic hydroxyl group (commonly but not necessarily in position 2) replaced by an amino group, systematically known as x-deoxy-x-monosaccharides. By way of example, D-glucosamine or 2-amino-2-deoxy-D-glucopyranose is an amino sugar. Other illustrative amino sugars include but are not limited to erythrosamine, threosamine, ribosamine, arabinosamine, xylosamine, lyxosamine, allosamine, altrosamine, glucosamine, mannosamine, idosamine, galactosamine, talosamine, and their derivatives. The amino sugars include both aldose and ketose sugars. Additionally, the amino sugars may be of a straight-chain structure; however, the aldehyde or ketone group of the amino sugar may react with a hydroxyl group on a different carbon atom to form a hemiacetal or hemiketal, in which case there is an oxygen bridge between the two carbon atoms, forming a heterocyclic ring. Amino sugar rings with five and six atoms are called furanose and pyranose forms, respectively and exist in equilibrium with their corresponding straight-chain form. It should be noted that the ring form has one more optically active carbon than the straight-chain form, and so has both an α and a β form, which interconvert in equilibrium. The term "amino sugar" also means glycosylamines, amino sugars where the nitrogen is substituted with a functional group other than H. Illustrative examples of glycosylamines include N-acetylglucosamine, N-methylglucosamine.

The term "metal" as used herein means any alkaline, alkaline earth, transition, rare earth, basic, and semi-metals which can coordinate with a ligand. Representative metals include the transition metals, lanthanide, and actinide metals. In more particular embodiments, the metal has d-orbitals capable of interacting with a ligand. The oxidative state of the metal can vary from 0 to 8. In some embodiments the oxidative state of the metal can vary from 1 to 7. In still other embodiments the oxidative state of the metal can vary from 1 to 4. In some embodiments, the oxidative state of the metal can vary from 1 to 2 while in other embodiments, the oxidative state of the metal can vary from 3 to 4.

The term "nutritionally acceptable metal" as used herein means metals that are known to be needed by living organisms, particularly plants and mammals, including humans. Metals such as boron, calcium, chromium, cobalt, copper, iron, magnesium, manganese, potassium, selenium, vanadium and zinc are exemplary of nutritionally acceptable metals.

The terms "hydrate" or "n-hydrate" as used herein means a molecular entity with some degree of hydration, where n is an integer representing the number of waters of hydration, e.g., monohydrate, dihydrate, trihydrate, tetrahydrate, pentahydrate, hexahydrate, septahydrate, octahydrate, nonahydrate, etc.

The term "saturated hydroxylated carboxylic acid" as used herein means an organic molecule possessing one or more carboxylic acid radicals or groups and one or more hydroxyl radicals or groups and lacks units of unsaturation such as olefins. A subset of saturated hydroxylated carboxylic acids are the carbohydrates where the ketone, aldehyde, and/or an alcohol has been oxidized to a carboxylic acid, including the aldonic acids (i.e., gluconic acid), uronic acids (i.e., glucuronic acid), and aldaric acids, (i.e., glucaric acid). Other examples of saturated hydroxylated carboxylic acids include those of an α-hydroxylated carboxylic acid, such as glycolic acid, lactic acid, malic acid, tartaric acid, citric acid, methyllactic acid, glyceric acid, α-hydroxybutanoic acid, α-hydroxhexanoic acid, α-hydroxyheptanoic acid or α-hydroxyoctanoic acid. Still other examples of saturated hydroxylated carboxylic acids are those of the β-hydroxylated acid, such as 3-hydroxybutyric acid. Saturated hydroxylated carboxylic acids useful in the invention exclude unsaturated forms like ascorbic acid. Particular saturated hydroxylated carboxylic acids are those which are of biological importance such as gluconic acid.

The term "matrix stabilizing salt" as used herein means a buffering composition which assists in preserving the oxidation state of the metal in a metal chelate. Examples of buffering agents include alkaline and alkaline earth metal salts of sulfates and organic carboxylic acids such as carbonates, citrates, malates, and succinates. Additional examples include magnesium sulfate and magnesium sulfate n-hydrate. It is contemplated that the matrix stabilizing salt can also include the alkaline and alkaline earth metal salts of the halogens when added as a reagent or generated in situ. In another aspect, the buffering agents may include alkaline and alkaline earth metal salts of carboxylates, halides, and sulfonates.

The term "chondroitin" as used herein means any of several glycosaminoglycans occurring in sulfated form in various tissues (as cartilage and tendons).

The term "glycosaminoglycans" as used herein means any of any of a group of polysaccharides that contain amino sugars. Glycosaminoglycans can also form complexes with proteins.

In one aspect of the invention, chelate complexes are described comprising a metal, one or more amino sugar ligands and one or more saturated hydroxylated carboxylic acid ligands, and nutritionally acceptable salts thereof. In some embodiments, the saturated hydroxylated carboxylic acid ligand is an aldonic acid, uronic acid, or aldaric acid. In embodiments where there is more than one saturated hydroxylated carboxylic acid ligand, the ligands may be homogeneous (each ligand is the same molecule) or heterogeneous (the ligands are different molecules).

In another aspect of the invention, compounds of the invention include chelates of a metal, an amino sugar, and a saturated hydroxylated carboxylic acid, or a nutritionally acceptable salt thereof. In some embodiments, the metal may be selected from magnesium, calcium, copper, zinc, iron, chromium, cobalt, molybdenum, selenium, and manganese. One embodiment involves a chelate where the metal is manganese. In embodiments where there is more than one amino sugar ligand, the ligands may be homogeneous (each ligand is the same molecule) or heterogeneous (the ligands are different molecules). In some embodiments, the amino sugar is selected from the group consisting of glucosamine, galactosamine, mannosamine, neuraminic acid, muramic acid, and glucuronamide. A particular example involves an amino sugar chelate of a metal where glucosamine is the amino sugar. In some embodiments, the saturated hydroxylated carboxylic acid is gluconic acid. In some embodiments, the stabilizing matrix salt is selected from the group consisting of alkaline and alkaline earth metal salts of sulfates and organic carboxylic acids such as carbonates, citrates, malates, and succinates. A particular embodiment involves an amino sugar chelate of a metal where the stabilizing matrix salt is magnesium sulfate and hydrochloric acid. In another embodiment, an amino sugar chelate of manganese where the metal is manganese, the amino sugar is glucosamine, and the saturated hydroxylated carboxylic acid is gluconic acid.

In another aspect of the invention, compounds of Formula 1 are described:

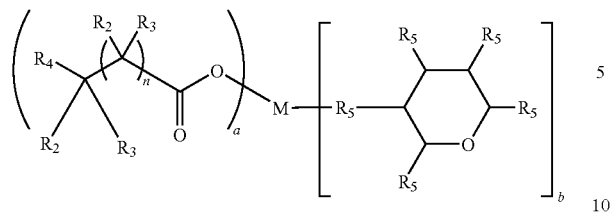

where M is a metal. $R_2$ and $R_3$ are independently selected from H, OH, and hydroxyl substituted $C_1$-$C_8$ alkyl, $R_4$ is selected from H, $CO_2H$, OH, and hydroxyl substituted $C_1$-$C_8$ alkyl. Each $R_5$ is independently selected from H, OH, $NH_2$, and hydroxyl substituted $C_1$-$C_8$ alkyl, wherein at least one $R_5$ is $NH_2$. In one aspect, a is from 0-6. In another aspect, a is from 1-6. In another aspect, a is from 1-4. In still another aspect, a is from 1-2. In another aspect, b is from 0-6. In another aspect, b is from 1-6. In still another aspect, b is from 1-4. In yet another aspect, b is from 1-2. In another aspect, n is from 1 to 8. In another aspect the compounds may be nutritionally acceptable salts of the compounds discussed above.

In yet aspect of the invention, compounds of Formula 2 are described:

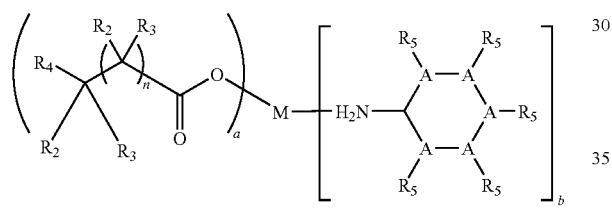

where M is a metal. $R_2$ and $R_3$ are independently selected from H, OH and hydroxyl substituted $C_1$-$C_8$ alkyl, $R_4$ is selected from H, $CO_2H$, OH, and hydroxyl substituted $C_1$-$C_8$ alkyl. Each $R_5$ is independently selected from H, OH, and hydroxyl substituted $C_1$-$C_8$ alkyl. A is selected from CH and O. It should be appreciated that when A is O then $R_5$ is absent and when $R_5$ is CH, $R_5$ is present. In one aspect, a is from 0-6. In another aspect, a is from 1-6. In yet another aspect, a is from 1-4. In still another aspect, a is from 1-2. In another aspect, b is from 0-6. In another aspect, b is from 1-6. In still another aspect, b is from 1-4. In yet another aspect, b is from 1-2. In another aspect, n is from 1 to 8. In another aspect the compounds may be nutritionally acceptable salts of the compounds discussed above.

In some embodiments where a is greater than one, there may be more than one type of saturated hydroxylated carboxylic acid. In some embodiments where b is greater than one, there may be more than one type of amino sugar ligand.

In some embodiments, M is selected from the group consisting of magnesium, calcium, copper, zinc, iron, chromium, cobalt, molybdenum, selenium, and manganese. In a particular example, M is manganese. In some embodiments, $R_2$ and $R_3$ are independently selected from H and OH. In some embodiments, a is 2. In some embodiments, M is a manganese, each $R_2$ is OH, each $R_3$ is H, $R_4$ is $CH_2CH_2OH$, $R_5$ is independently selected from H, OH, hydroxyl substituted $C_1$-$C_8$ alkyl, or absent, each A is independently selected from CH, $CH_2$ and O, a is from 1-2, b is from 1-2 and n is 3.

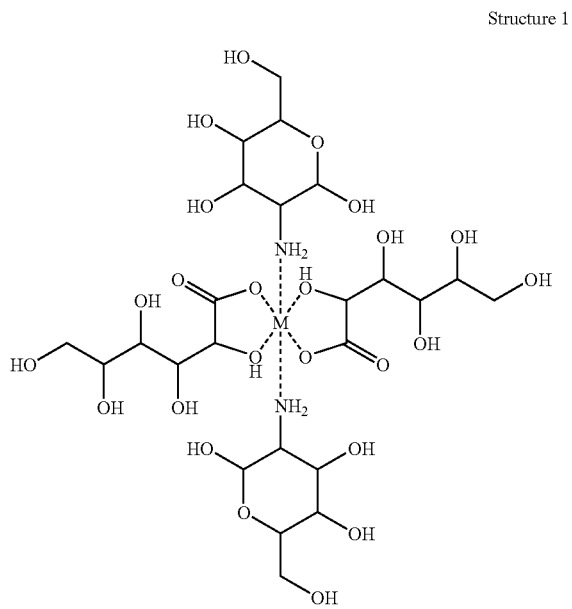

Structure 1

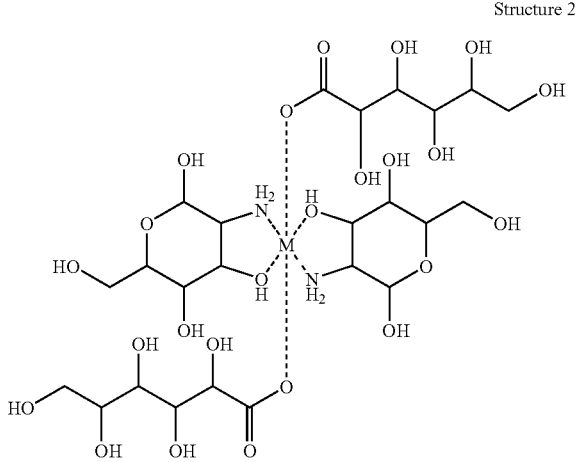

Structure 2

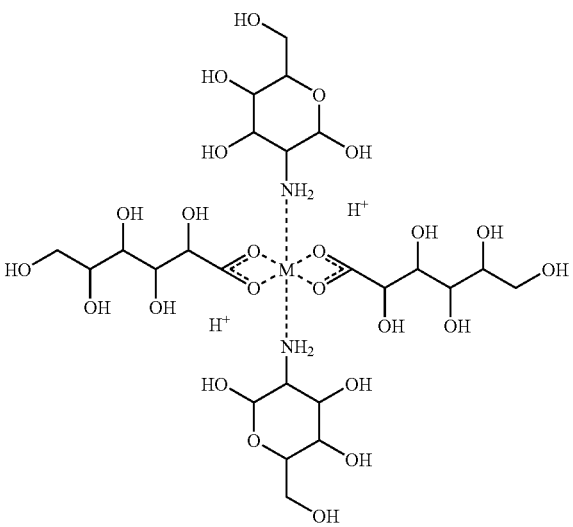

Structure 3

-continued

Structure 4

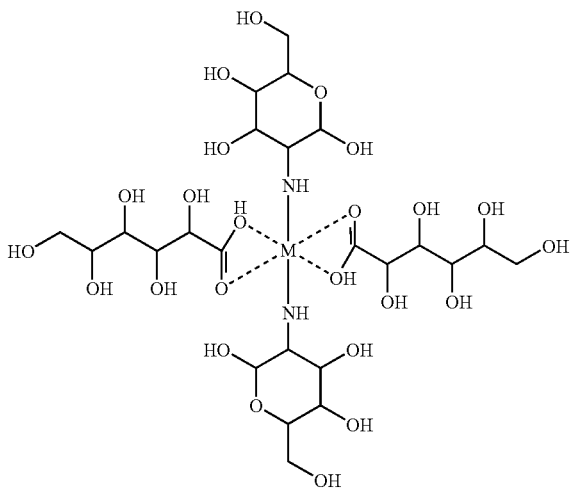

In still another aspect of the amino sugar chelates, the chelate of Formula 2 may have the structure of any of Structures 1, 2, 3, 4 or a representation that is a combination of Structures 1 to 4. For example, manganese glucosamine gluconate chelate may have a ligand (a+b) to metal molar ratio of 2:1 (a=1, b=1), 3:1 (a=2, b=1), or 4:1 (a=2, b=2). Additionally, other ligand to metal molar ratios include glucosamine to calcium at 4:1 (a=2, b=2); glucosamine to zinc at 4:1 (a=2, b=2); glucosamine to chromium at 4:1 (a=2, b=2), 3:1 (b=3); glucosamine to manganese at 4:1 (b=2); and glucosamine to iron a 4:1 (a=2, b=2), 5:1 (a=2, b=3). The oxidation state of the metal will influence the number of suitable ligand binding sites necessary to satisfy the chelate.

It is important to note that the bonds when depicted between the metal (M) and nitrogen of the amine group, between the metal and an oxygen of a carboxyl group, and between the metal and a hydroxyl group as shown and described should not be strictly construed to represent only an ionic bond, a covalent bond, or a coordinate covalent bond. While not being bound to any particular theory, it is theorized that possible physical structures of the chelates of the invention may be any one of Structures 1-4, or a combination of such structures. The structures depicted as Structures 1-4 should convey that all of the bonds to the metal from a heteroatom can be of a ionic, covalent, coordinate covalent nature or some intermediate combination of those bond natures.

For optimal absorption through the intestinal tract, the net electrical charge of the chelate is zero. The value of at least one of a and b is usually equal to the valence of the metal so as to balance the electrostatic charge of the species to zero. In some examples, the value of at least one of a and b can be greater than the valence of the metal, in which case, one or more $H^+$ may be present and associated with the amino sugar and/or the saturated hydroxylated carboxylic acid. Generally, any positive charge on the metal ion is neutralized by electrons contributed by one or more of the ligands in formation of a heterocyclic chelate ring. In some examples, the value of at least one of a and b will be less than the valence of the metal, in which case, one or more anions may be present and associated with the metal as another ligand.

In still another aspect of the invention, an amino sugar chelate is described with one or more amino sugar ligands, one or more saturated hydroxylated carboxylic acid ligands, and a metal, where the ligands and the metal have a molar ratio of from 1:1 to 4:1. In some examples, a glucosamine chelate is described with one or more glucosamine ligands and manganese gluconate, where the glucosamine ligand to manganese ratio is 2:1.

In yet another aspect of the invention, an amino sugar chelate is described where the amino sugar chelate is defined by the formula: $(C_6H_{13}NO_5)_bM(C_6H_{12}O_7)_a$, where a is from 1 to 4, and b is from 1 to 4. In some embodiments, the amino sugar chelate formula value for a is 1 and b is 2. In some embodiments, the amino sugar chelate formula value for a is 2 and b is 2.

In still another aspect of the invention, a composition comprising a metal, an amino sugar, a saturated hydroxylated carboxylic acid, and a stabilizing matrix salt is described. In some embodiments, the metal is selected from the group consisting of magnesium, calcium, copper, zinc, iron, chromium, cobalt, molybdenum, selenium, and manganese. In particular embodiments, manganese is a nutritionally useful metal. In some embodiments, the composition includes an amino sugar selected from the group consisting of glucosamine, galactosamine, mannosamine, neuraminic acid, muramic acid, and lucuronamide. In particular embodiments, glucosamine is a nutritionally useful amino sugar. In particular embodiments, gluconic acid is a nutritionally useful saturated hydroxylated carboxylic acid. In some embodiments, the stabilizing matrix salt is selected from the group consisting of alkaline and alkaline earth metal salts of sulfates and organic carboxylic acids such as carbonates, citrates, malates, and succinates. In particular embodiments, magnesium sulfate and hydrochloric acid are nutritionally useful matrix stabilizing salts.

Optionally, the compositions may include vitamin C.

Optionally, the compositions may include chondroitin.

In yet another aspect of the invention, compositions of the invention are those with compounds of Formula 1 and a stabilizing matrix salt. In some embodiments, M is selected from the group consisting magnesium, calcium, copper, zinc, iron, chromium, cobalt, molybdenum, selenium, and manganese. In particular examples, manganese is a nutritionally useful metal. In some examples, $R_2$ and $R_3$ are independently selected from H and OH. In some examples, a is 2.

In still another aspect of the invention, compositions of the invention are those with compounds of Formula 3

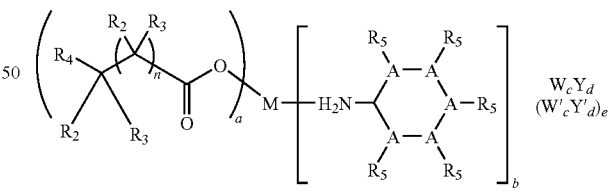

where M, $R_2$, $R_3$, $R_4$, $R_5$, A, a, b, and n have the meaning given for Formula 2; and, in addition, W and W' are independently selected from the alkaline and alkaline earth metals and H, Y and Y' are independently selected from the inorganic anions, and e is from 0 to 2. Illustrative examples of inorganic anions include but are not limited to halogen, sulfate, and anionic organic carboxylic acids such as carbonate, citrate, malinate, and succinate. Components $W_cY_d$ and $W'_cY'_d$ alone or in combination constitute a stabilizing matrix salt. When e is 0, then the stabilizing matrix salt is homogenous. When is 1 or greater, then the stabilizing matrix salt is heterogeneous. Generally, the stabilizing matrix salt is not an acid, but can be an acid salt or buffering agent. Furthermore, the matrix stabilizing salt can become an acid generated in situ when a composition is formed.

In the compounds and compositions described above, M is a metal. Particular metals are those selected from the group consisting of magnesium, calcium, copper, zinc, iron, chromium, cobalt, molybdenum, selenium, and manganese. In particular examples, manganese is a nutritionally useful metal. The oxidation state of the metal can very from 0 to 8 depending upon the particular metal. For most metals, the oxidation state will be from 1 to 7 and alternatively from 2 to 4.

The amino sugar (the bracketed species in Formulas 1-3) can be a ligand and can be present in a ratio of ligand to metal of from about 1:1 to 3:1, alternatively 1:1 to 2:1, and also alternatively 2:1. The saturated hydroxylated carboxylic acid (the parenthetical species in Formulas 1-3) can also be a ligand and can be present in a ratio of ligand to metal of from about 1:1 to 5:1, alternatively, 1:1 to 4:1, also alternatively 1:1 to 3:1, and also alternatively 1:1 to 2:1.

In yet another aspect of the invention, a method for preparing amino sugar chelates is described comprising the steps of combining a saturated hydroxylated carboxylic acid with a solution, combining a metal or a metal salt with a solution, combining an amino sugar with a solution where the solution has a pH of about 1 to about 7.5.

In another aspect of the invention, a method of preparing an amino sugar chelate is described comprising the steps of combining a saturated hydroxylated carboxylic acid and a metal source in solution to obtain a metal saturated hydroxylated carboxylic acid salt, and combining an amino sugar with the solution.

In still another aspect of the invention, a method of preparing an amino sugar chelate is described comprising the step of mixing a metal source, a saturated hydroxylated carboxylic acid and an amino sugar in a solution at a pH in the range of about 1 to about 7.5. In some examples of the methods described above, the method also includes the step of adding a matrix stabilizing salt with the solution. In some embodiments of the previously described methods, the methods include the step of adding a buffering agent selected from the group consisting of alkaline and alkaline earth metal salts of sulfates and organic carboxylic acids such as carbonates, citrates, malates, and succinates to obtain a matrix of the buffering agent and the amino sugar chelate. In some embodiments of the previously described methods, the methods include removing the solvent from the solution.

Optionally, vitamin C may be added to the mixture.

Optionally, chondroitin may be added to the mixture.

In yet another aspect of the invention, products made by the methods described above are disclosed. Some examples of such products include beverages, beverage mixes, granola bars, and other suitable consumable foods.

Generally, the method of preparing the chelates of the present invention is as follows. A metal source is combined in a suitable solution. The metal source can be a metal salt or a metal. In some instances, the metal source can be dissolved in water or solubilized in an acidic solution. If an acidic solution is required to dissolve the metal source, acids such as acetic, citric, lactic, malic, hydrochloric, sulfuric, tartaric, maleic, and saturated hydroxylated carboxylic acids may be used. If a metal salt is used that is soluble in water, it may not be required to use an acidic solution, though it may be desired. A saturated hydroxylated carboxylic acid may be used to acidify the solution. By way of example, if magnesium is the metal to be chelated, magnesium sulfate, magnesium citrate, magnesium chloride, and/or magnesium oxide may be used as the metal source. The magnesium source will either be dissolved in water or acidified in an acidic solution. Also by way of example, if manganese is the metal to be chelated, elemental manganese may be used as a metal source. The manganese will be dissolved in saturated hydroxylated carboxylic acid acidified water and undergo an oxidation reduction reaction to form the manganese salt of the saturated hydroxylated carboxylic acid.

To the solution of saturated hydroxylated carboxylic acid metal salt, an amino sugar ligand is added. If the pH level is basic (i.e., if it is greater than about 7.5) a pH adjuster may be added. pH adjusters may include citric acid, malic acid, acetic acid, hydrochloric acid, tartaric acid, lactic acid, sulfuric acid, and naturally occurring amino acids such as aminobutyric acid, aspartic acid and glutamic acid among others.

If the metal is prone to undergo further oxidation when left exposed to air, it may be necessary to add buffering salts to the solution prior to drying. For example, if manganese is the desired metal for the chelate, Epsom salts may be added to the solution prior to removal of solvent and drying.

In one method, the chelate of Formula 2 is formed, as depicted in Scheme 1, by reacting the saturated hydroxylated carboxylic acid in solution with a desired metal to form a salt of the metal and saturated hydroxylated carboxylic acid (MSHCA). This may be done through an oxidation-reduction reaction in water, ion exchange, or mixing the saturated hydroxylated carboxylic acid with a metal salt and driving off the anion from the metal salt using various techniques available to one skilled in the art including precipitation.

The MSHCA salt is then mixed with an amino sugar at a temperature from about 0 to about 100° C., alternatively from about 20-45° C., and also alternatively from about 25 to about 37° C. One or more matrix stabilizing salts may then be added to the solution. The solvent is removed and the resulting slurry dried.

Scheme 1.

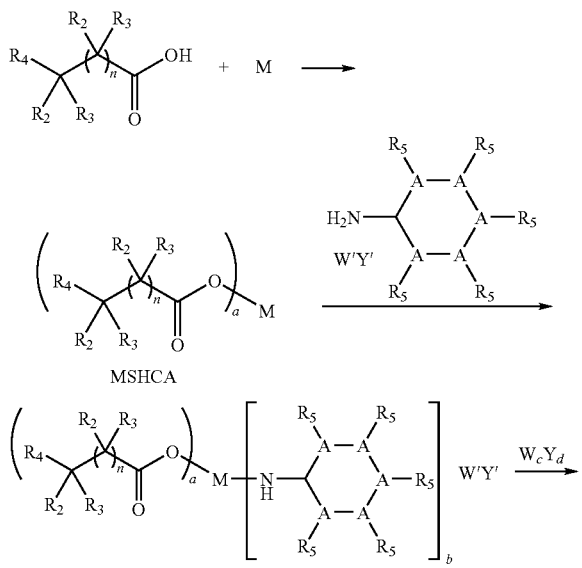

-continued

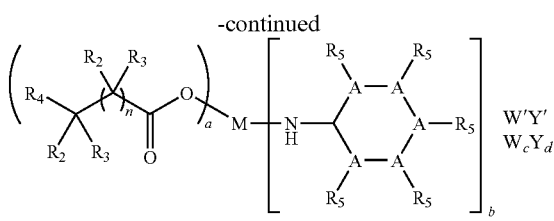

The amino sugar may be provided from a variety of forms including the acid salts selected from the group consisting of HCl, HBr, HI, HCN, $H_2SO_4$, HCOOH, $CH_3COOH$, $H_3BO_3$, $H_2CO_3$, and corresponding alkaline and alkaline acid salts such as potassium or sodium sulfate and mixtures of those acids and salts. Free glucosamine may be prepared and used from the aforementioned salts of glucosamine. Particularly the amino sugar is provided in the form of an acid salt selected from the group consisting of HCl, $H_2SO_4$, and $CH_3COOH$. The metal may be provided by a member selected from the group consisting of magnesium, calcium, copper, zinc, iron, chromium, cobalt, molybdenum, selenium and manganese in elemental form or in the form of chlorides, bromides, sulfates, oxides, hydroxides, carbonates and/or bicarbonates. The metal can be in its ground valence of 0.

When removing solvent from the solution, it should be understood that not all solvent must be removed. When the solvent is water, it is generally sufficient to remove essentially all of the water so that the resulting material is less than about 10% water. In some embodiments, the resulting material is less than about 1% water. In some embodiments, the resulting material is substantially free of water or less than about 0.1% water. When the solvent is something other than water (i.e., an organic solvent), it is generally sufficient to remove the solvent so that less than about 0.1% of the material is solvent. Alternatively, in some embodiments the solvent should be less than about 0.01%. Typically, the amount of solvent remaining in the material should be such that consumption of the material does not result in adverse health conditions, the material is stable, meets functional requirements, and is not subject to decomposition or microbial contamination.

The present invention is also drawn toward a method of administering an amino sugar chelate with a saturated hydroxylated carboxylic acid to a mammal. The steps include (a) formulating an effective amount of an amino sugar chelate with a saturated hydroxylated carboxylic acid into a nutritional supplement suitable for oral consumption; and (b) administering the nutritional supplement containing the amino sugar chelate to a mammal. The nutritional supplement may be in the form of tablets, food bars, drinks, dry drink mixes or other substances acceptable for oral consumption. Tablets may be chewable or non-chewable. Food bars may be in the form of energy bars, weight loss bars, snack bars, granola bars or combinations thereof. Drinks may be in the form of energy drinks, sports drinks, fruit drinks, citrus drinks, carbonated drinks, other suitable drink mediums or combinations thereof. Finally, the dry drink mixes may be in the form of a fruit mix and/or citrus mix or other particulate drink mixes.

The following examples illustrate compositions and methods of preparing amino sugar chelates with saturated hydroxylated carboxylic acid as well as various applications for which those chelates may be used.

EXAMPLES

Example 1

To a mixing tank, 580.4 pounds (70 gallons, 264.98 L) of water was heated to 35° C. 189.3 lbs (85.87 kg) of glucono-δ-lactone was added and stirred for 15 minutes at which time the solution appeared transparent and clear. 27.5 pounds (12.47 kg) of manganese metal was added to the solution slowly and stirred for 4 hours. 215.6 pounds (97.79 kg) of glucosamine HCl is added and stirred for 30 minutes. 116.2 pounds (52.71 kg) of magnesium sulfate heptahydrate was added and stirred for 30 minutes. The solution was dried with a spray drier outlet temperature at 70° C. The resulting white powder had a melting point of 73° C., with a yield of 93% after spray drying.

Example 2

To a mixing tank, 778.8 pounds of water were heated to 35° C. 178.1 lbs (80.78 kg) of glucono-δ-lactone was added and stirred for 15 minutes at which time the solution appeared transparent and clear. 54.9 pounds (24.9 kg) of manganese metal was added to the solution slowly and stirred for 4 hours. 192.1 pounds (87.14 kg) of citric acid was added to the solution slowly and stirred for one hour. 215.6 pounds (97.79 kg) of glucosamine HCl is added and stirred for 30 minutes. 123.2 pounds (55.88 kg) of magnesium sulfate heptahydrate was added and stirred for 30 minutes. The solution was dried with a spray drier outlet temperature at 70° C. The resulting white colored powder was obtained after spray drying.

Example 3

To a mixing tank, 488.6 pounds of water were heated to 35° C. 178.1 lbs (80.78 kg) of glucono-δ-lactone was added and stirred for 15 minutes at which time the solution appeared transparent and clear. 48.8 pounds (22.1 kg) of copper hydroxide was added to the solution slowly and stirred for 4 hours. 215.6 pounds (97.79 kg) of glucosamine HCl is added and stirred for 30 minutes. 123.2 pounds (55.88 kg) of magnesium sulfate heptahydrate was added and stirred for 30 minutes. The solution was dried with a spray drier outlet temperature at 70° C. The resulting turquoise colored powder was obtained at a yield of 90% after spray drying.

Example 4

To a mixing tank, 540.7 pounds of water were heated to 35° C. 178.1 lbs (80.78 kg) of glucono-δ-lactone was added and stirred for 15 minutes at which time the solution appeared transparent and clear. 62.7 pounds (28.4 kg) of zinc carbonate was added to the solution slowly and stirred for 4 hours. 215.6 pounds (97.79 kg) of glucosamine HCl is added and stirred for 30 minutes. 123.2 pounds (55.88 kg) of magnesium sulfate heptahydrate was added and stirred for 30 minutes. The solution was dried with a spray drier outlet temperature at 70° C. The resulting créme colored powder was obtained at a yield of 94% after spray drying.

Example 5

A chocolate chew with manganese glucosamine was prepared by combining sugar, corn syrup, shortening and cocoa.

The mixture of ingredients was heated to approximately 135° C. The mixture was removed from heat and condensed milk and manganese glucosamine were added. The combined ingredients were mixed using an electric mixer for approximately one minute. To the blended mixture, vanilla was added and the blend of ingredients was again mixed. The blended mixture was poured onto wax paper and formed into a desired shape. The chocolate chews were allowed to harden. The relative proportions of the ingredients are listed in Table 1.

TABLE 1

| Ingredients | % Product | Desired g |
| --- | --- | --- |
| Sugar | 45.31 | 212.00 |
| Light corn syrup | 32.06 | 150.00 |
| Shortening | 6.41 | 30.00 |
| Cocoa | 1.60 | 7.50 |
| Condensed milk | 10.90 | 51.00 |
| Mn glucosamine | 0.64 | 3.00 |
| Glucosamine HCl | 2.56 | 12.00 |
| Vanilla | 0.51 | 2.40 |
| Total | 100.00 | 467.90 |

Example 6

A granola bar with manganese glucosamine was prepared by melting butter and honey to a smooth consistency. To the butter and honey mixture, sugar was added and dissolved while mixing. The mixture was heated for 1-2 minutes to create a caramel sauce. To the caramel sauce, the following ingredients were added: oats (jumbo), crisp rice, ground cinnamon, pecan halves, raisins, dates, and ground almonds. The resulting combination was mixed and transferred to a baking dish and pressed into individual bars. The bars were baked for 15 minutes at 375° F. The bars were allowed to cool. A bowl of chocolate chips were melted, and manganese glucosamine and glucosamine hydrochloride was added to the bowl. The chocolate and glucosamine supplements were mixed and then poured on the granola bars. The relative proportions of the ingredients are listed in Table 2.

TABLE 2

| Ingredients | % Product | Desired g |
| --- | --- | --- |
| Butter | 10.42 | 175.00 |
| Honey | 8.93 | 150.00 |
| Sugar | 14.88 | 250.00 |
| Oats (jumbo) | 20.83 | 350.00 |
| Crisp rice | 1.79 | 30.00 |
| Ground cinnamon | 0.18 | 3.00 |
| Pecan halves | 4.46 | 75.00 |
| Raisins | 6.84 | 115.00 |
| Dates | 6.84 | 115.00 |
| Ground almonds | 2.98 | 50.00 |
| Milk chocolate chips | 17.86 | 450.00 |
| Mn glucosamine | 1.14 | 19.20 |
| Glucosamine HCl | 2.86 | 48.00 |
| Total | 100.00 | 1830.20 |

Example 7

A pineapple glucosamine beverage mix was prepared by dry blending sucrose, manganese glucosamine, glucosamine hydrochloride, gum Arabic spray dry fcc powder—TIC gums, citric acid (USP grade), pineapple flavor (Mane Inc.), and natural yellow coloring (colorMaker formula #6658) in the proportions listed in Table 3.

TABLE 3

| Ingredients | % Product | Desired g |
| --- | --- | --- |
| Sucrose | 84.20 | 26.00 |
| Glucosamine HCl | 6.48 | 2.00 |
| Gum Arabic Spray Dry FCC Powder - TIC Gums | 4.21 | 1.30 |
| Mn Glucosamine - Albion | 2.59 | 0.80 |
| Citric Acid - USP grade | 1.94 | 0.60 |
| Pineapple flavor - Mane Inc. | 0.32 | 0.10 |
| Natural yellow - colorMaker (formula #6658) | 0.26 | 0.08 |
| Total | 100.00 | 30.88 |

Example 8

A liquid beverage was prepared using the dry blend beverage mixture of example 7, which was added to 8 fluid ounces of water. The mixture was shaken vigorously until the dry blend was dissolved. The resulting beverage can also be chilled before serving.

Example 9

An orange glucosamine/chondroitin beverage mix was prepared by dry blending sucrose, manganese glucosamine, glucosamine hydrochloride, chondroitin sulfate sodium (OptaFlex #621), gum Arabic spray dry fcc powder—TIC gums, citric acid (USP grade), orange flavor (Mane Inc.), and natural orange coloring in the proportions listed in Table 4.

TABLE 4

| Ingredients | % Product | Desired g |
| --- | --- | --- |
| Sucrose | 77.50 | 26.00 |
| Glucosamine HCl | 5.96 | 2.00 |
| Chondroitin sulfate sodium - OptaFlex (#621) | 4.02 | 1.35 |
| Gum Arabic Spray Dry FCC Powder - TIC Gums | 3.87 | 1.30 |
| Orange flavor - Mane Inc. | 2.98 | 1.00 |
| Citric acid - USP grade | 2.98 | 1.00 |
| Mn Glucosamine - Albion | 2.38 | 0.80 |
| Color - natural orange | 0.30 | 0.10 |
| Total | 100.00 | 33.55 |

Example 10

A liquid beverage was prepared using the dry blend beverage mixture of example 9, which was added to 8 fluid ounces of water. The mixture was shaken vigorously until the dry blend was dissolved. The resulting beverage can also be chilled before serving.

Example 11

A strawberry glucosamine/chondroitin beverage mix was prepared by dry blending sucrose, manganese glucosamine, glucosamine hydrochloride, gum Arabic spray dry fcc powder—TIC gums, citric acid (USP grade), N&A strawberry flavor (WILD FAGL795), and FD&C Art Red #40 (WILD FAGL796) in the proportions listed in Table 5.

TABLE 5

| Ingredients | % Product | Desired g |
| --- | --- | --- |
| Sucrose | 84.20 | 26.00 |
| Glucosamine HCl | 6.48 | 2.00 |
| Gum Arabic Spray Dry FCC Powder - TIC Gums | 4.21 | 1.30 |
| Mn Glucosamine - Albion | 2.59 | 0.80 |
| Citric acid - USP grade | 1.94 | 0.60 |
| N&A Strawberry flavor - WILD FAGL795 | 0.32 | 0.10 |
| FD&C Art Red #40 - WILD FAGL796 | 0.26 | 0.08 |
| Total | 100.00 | 30.88 |

Example 12

A liquid beverage was prepared using the dry blend beverage mixture of example 11, which was added to 8 fluid ounces of water. The mixture was shaken vigorously until the dry blend was dissolved. The resulting beverage can also be chilled before serving.

Example 13

A pineapple glucosamine beverage mix was prepared by dry blending xanthan gum, potassium benzoate, sugar, Acesulfame K, malitol, malic acid, MSM, collagen, chondroitin, manganese glucosamine, glucosamine hydrochloride, vitamin C, vitamin D, pineapple flavor and natural yellow coloring in the proportions listed in Table 6.

TABLE 6

| Ingredients | Mw | % Product | Desired g |
| --- | --- | --- | --- |
| Xanthan Powder (Ticaxan) | | 0.01 | 0.01 |
| K Benzoate (Probenz) | 160.21 | 0.19 | 0.14 |
| Sugar | 342.30 | 37.03 | 27.43 |
| Ace-K | 201.20 | 0.03 | 0.0195 |
| Maltitol | 344.00 | 37.01 | 27.41 |
| Malic Acid | 134.09 | 0.32 | 0.2412 |
| MSM | 94.13 | 3.38 | 2.50 |
| Collagen | | 0.34 | 0.25 |
| Chondroitin | | 8.10 | 6.00 |
| Mn Glucosamine | | 2.70 | 2.00 |
| Glucosamine HCl | 215.63 | 10.12 | 7.50 |
| Vitamin C (ascorbic acid) | | 0.41 | 0.300 |
| Vitamin D3 | | 0.00 | 0.00005 |
| Flavor (pineapple) | | 0.16 | 0.120 |
| Color (natural yellow) | | 0.20 | 0.15 |
| Total | | 100.00 | 74.07075 |

Example 14

A liquid beverage was prepared using the dry blend beverage mixture of example 13, which was added to 8 fluid ounces of water. The mixture was shaken vigorously until the dry blend was dissolved. The resulting beverage can also be chilled before serving.

It is to be understood that the foregoing descriptions of embodiments of the present invention are exemplary and explanatory only, are not restrictive of the invention, as claimed, and merely illustrate various embodiments of the invention. It will be appreciated that other particular embodiments consistent with the principles described in the specification but not expressly disclosed may fall within the scope of the claims.

We claim:

1. A compound of the formula:

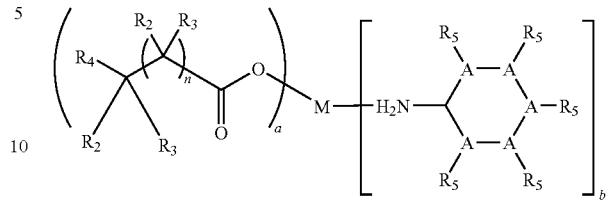

wherein M is a nutritionally acceptable metal, $R_2$ and $R_3$ are independently selected from H, OH and hydroxyl substituted $C_1$-$C_8$ alkyl, $R_4$ is selected from H, $CO_2H$, OH, and hydroxyl substituted $C_1$-$C_8$ alkyl, each $R_5$ is independently selected from H, OH, hydroxyl substituted $C_1$-$C_8$ alkyl, or absent, A is selected from CH and O, a is from 1-6, b is from 1-6, n is from 1 to 8, wherein M is a nonferrous metal.

2. A compound of the formula:

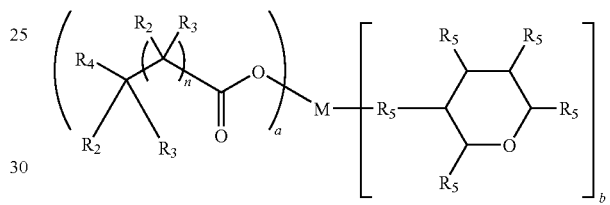

wherein M is a nutritionally acceptable metal, $R_2$ and $R_3$ are independently selected from H, OH, and hydroxyl substituted $C_1$-$C_8$ alkyl, $R_4$ is selected from H, $CO_2H$, OH, and hydroxyl substituted $C_1$-$C_8$ alkyl, each $R_5$ is independently selected from H, OH, $NH_2$, and hydroxyl substituted $C_1$-$C_8$ alkyl, a is from 1-6, b is from 1-6, n is from 1 to 8, wherein M is a nonferrous metal and wherein only one $R_5$ is $NH_2$.

3. A compound of claim 1, wherein M is selected from the group consisting of magnesium, calcium, copper, zinc, chromium, cobalt, molybdenum, selenium, and manganese.

4. A compound of claim 1, wherein M is manganese.

5. A compound of claim 1, wherein $R_2$ and $R_3$ are independently selected from H and OH.

6. A compound of claim 1, wherein a is 2.

7. A compound of claim 1, wherein M is a manganese, each $R_2$ is OH, each $R_3$ is H, $R_4$ is $CH_2CH_2OH$, $R_5$ is independently selected from H, OH, hydroxyl substituted $C_1$-$C_8$ alkyl, or absent, each A is independently selected from CH, $CH_2$ and O, a is from 1-6, b is from 1-6 and n is 3.

8. An amino sugar chelate comprising one or more amino sugar ligands, one or more saturated hydroxylated carboxylic acid ligands, and a nutritionally acceptable metal, wherein at least one of the one or more amino sugar ligands is glucosamine, and wherein the metal is manganese, and wherein the one or more saturated hydroxylated carboxylic acid ligands is gluconic acid, and wherein the glucosamine ligand to manganese ratio is 2:1, wherein the nutritionally metal is nonferrous.

9. An amino sugar chelate comprising one or more amino sugar ligands, one or more saturated hydroxylated carboxylic acid ligands, and a nutritionally acceptable metal, wherein the ligand to metal molar ratio is from 2:1 to 4:1, wherein the amino sugar chelate is defined by the formula:

$(C_6H_{13}NO_5)_bM(C_6H_{12}O_7)_a$, wherein a is from 1 to 6, and b is from 1 to 6, wherein the nutritionally acceptable metal is nonferrous.

10. The amino sugar chelate of claim 9, wherein a is 1 and b is 2.

11. The amino sugar chelate of claim 9, wherein a is 2 and b is 2.

12. A composition comprising a compound of the formula:

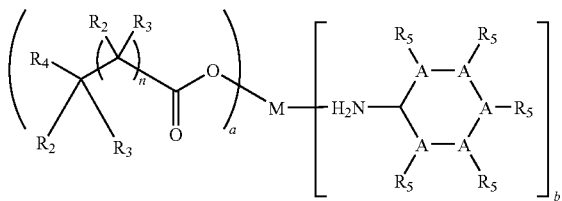

wherein M is a nutritionally acceptable metal, $R_2$ and $R_3$ are independently selected from H, OH and hydroxyl substituted $C_1$-$C_8$ alkyl, $R_4$ is selected from H, $CO_2H$, OH, and hydroxyl substituted $C_1$-$C_8$ alkyl, each $R_5$ is independently selected from H, OH, hydroxyl substituted $C_1$-$C_8$ alkyl, or absent, A is selected from CH and O, a is from 1-6, b is from 1-6, n is from 1 to 8;
a stabilizing matrix salt;
chondroitin; wherein M is nonferrous.

13. A composition comprising a compound of the formula:

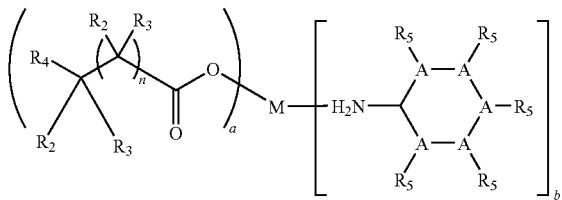

wherein M is a nutritionally acceptable metal, $R_2$ and $R_3$ are independently selected from H, OH and hydroxyl substituted $C_1$-$C_8$ alkyl, $R_4$ is selected from H, $CO_2H$, OH, and hydroxyl substituted $C_1$-$C_8$ alkyl, each $R_5$ is independently selected from H, OH, hydroxyl substituted $C_1$-$C_8$ alkyl, or absent, A is selected from CH and O, a is from 1-6, b is from 1-6, n is from 1 to 8;
a stabilizing matrix salt;
vitamin C; wherein M is nonferrous.

14. A composition comprising a compound of the formula:

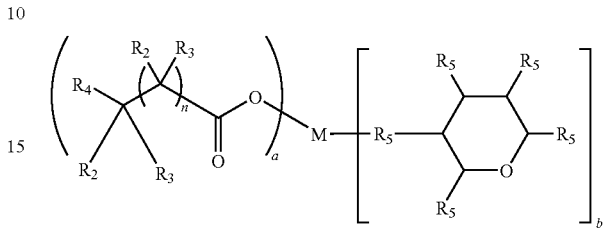

wherein M is a nutritionally acceptable metal, $R_2$ and $R_3$ are independently selected from H, OH, and hydroxyl substituted $C_1$-$C_8$ alkyl, $R_4$ is selected from H, OH, $CO_2H$, and hydroxyl substituted $C_1$-$C_8$ alkyl, each $R_5$ is independently selected from H, OH, hydroxyl substituted $C_1$-$C_8$ alkyl, or absent, each A is independently selected from CH, $CH_2$ and O, a is from 1-6, b is from 1-6, n is independently from 0 to 8, and a stabilizing matrix salt, wherein M is nonferrous.

15. The composition of claim 12, wherein M is selected from one or more of the group consisting of magnesium, calcium, copper, zinc, chromium, cobalt, molybdenum, selenium, and manganese.

16. The composition of claim 12, wherein M is manganese.

17. The composition of claim 12, wherein $R_2$ and $R_3$ are independently selected from H and OH.

18. The composition of claim 12, wherein a is 2.

19. The composition of claim 12, further comprising chondroitin.

20. The composition of claim 12, further comprising vitamin C.

* * * * *